United States Patent [19]
Fries

[11] Patent Number: 6,083,182
[45] Date of Patent: Jul. 4, 2000

[54] SUPPORT ARRANGEMENT FOR SUPPORTING THE ARM OF A PATIENT IN A BENT POSITION

[76] Inventor: Horst Fries, Pilotystr. 29, Nürnberg, Germany, 90408

[21] Appl. No.: 08/970,568

[22] Filed: Nov. 14, 1997

[30] Foreign Application Priority Data

Nov. 15, 1996 [DE] Germany ................. 296 19 777 U

[51] Int. Cl.[7] ................................................ A61F 5/00
[52] U.S. Cl. ................................. 602/4; 602/34
[58] Field of Search ................. 602/1, 4, 5, 70, 602/33–35, 60–62; 128/845, 846, 869, 878, 882

[56] References Cited

U.S. PATENT DOCUMENTS

| | | | |
|---|---|---|---|
| D. 273,516 | 4/1984 | Saal | 602/20 X |
| 2,549,809 | 4/1951 | Sanders | 602/4 |
| 2,847,002 | 8/1958 | Doumar | 602/4 |
| 3,199,509 | 8/1965 | Smith | 602/4 |
| 3,433,221 | 3/1969 | Kendall et al. | 602/4 |
| 3,923,050 | 12/1975 | Zeide et al. | 602/4 |

OTHER PUBLICATIONS

Doumar, Florence, A Postoperative Arm–Suspension Sling, The Journal of Bone and Joint Surgery, p. 908–909, Aug. 1956.

*Primary Examiner*—Richard J. Apley
*Assistant Examiner*—Denise Pothier

*Attorney, Agent, or Firm*—Merchant & Gould P.C.

[57] ABSTRACT

Support arrangement for supporting the arm of a patient in a bent position of the upper arm relative to the lower arm. The support arrangement includes a holding bag, which on an upper side is attachable in a hanging manner to a support. The holding bag forms a bottom side configured for the upper arm and forms a first side configured for the underside of the bent lower arm. The holding bag is made exclusively of textile-like material and consists of a flat cut, folded and sewn up on the upper and lower sides. A second side of the holding bag facing the upper arm is formed so as to be closeable, and at least one cord for closing the second side and at least one fastening cord for fastening the holding sack at its upper side are provided. The holding bag may be formed tapered at its width at least on the upper side. The holding bag may be formed open in the tapered region both on the side facing the upper arm and on the side turned away from the upper arm. At least one pair of cords may be provided, each pair consisting of one cord attached to each position of the holding bag. The pair of fastening cords may consist of a shorter and a longer fastening cord. A seam may be provided on the upper side and the pair of fastening cords may be formed of a one-piece cord led through on the underside of the seam. The holding bag is dimensioned in such a manner that a freedom of movement is ensured for the lower arm located within it. The holding bag may be formed double-layered over the entire side facing the upper arm. The holding bag may be formed double-layered in the open side-region of the side facing the lower arm. The tapered region may have a length that corresponds approximately to a third of the overall length of the holding bag.

9 Claims, 3 Drawing Sheets

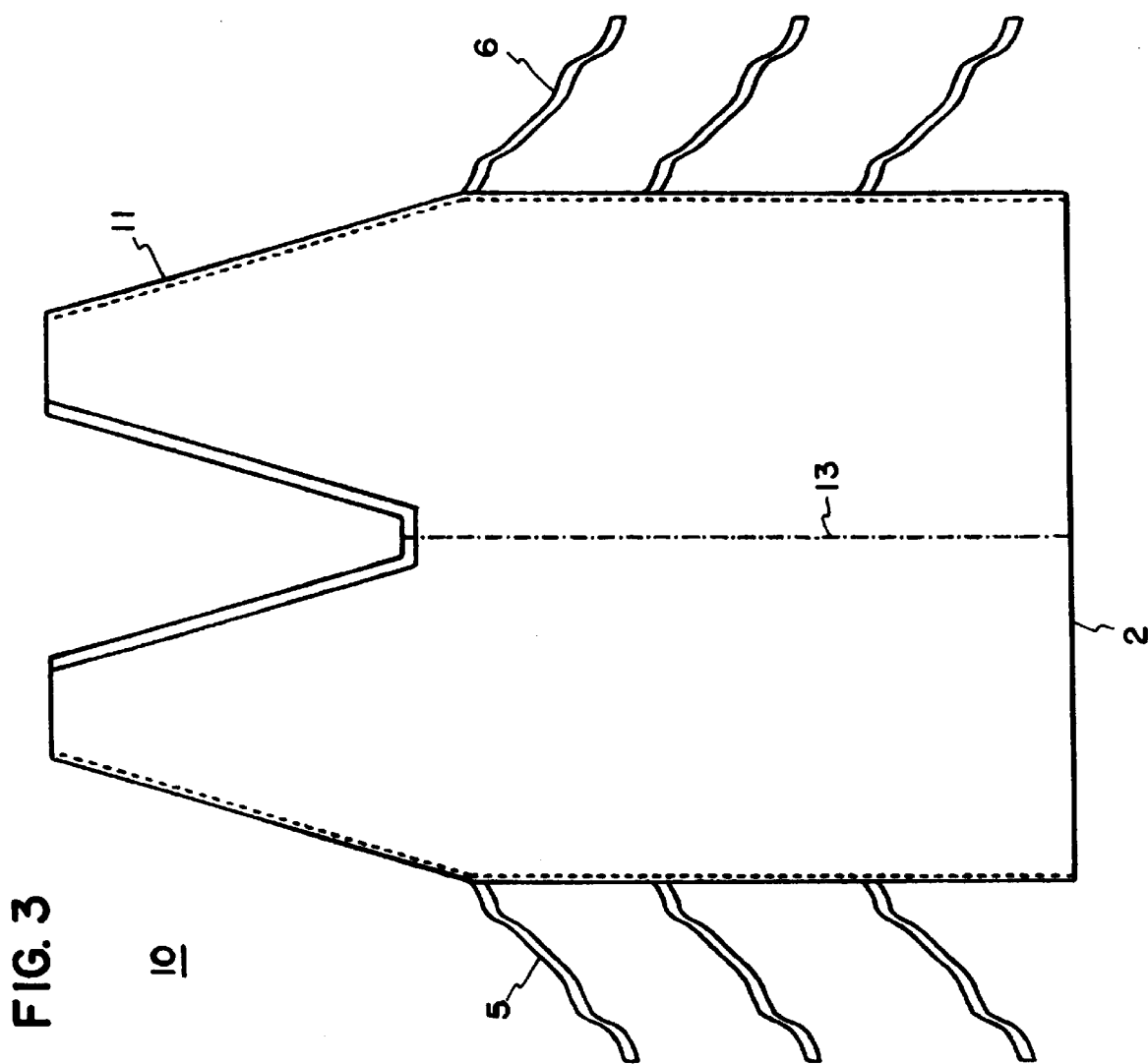

SUPPORT ARRANGEMENT FOR SUPPORTING THE ARM OF A PATIENT IN A BENT POSITION

FIELD OF THE INVENTION

The present innovation concerns a support arrangement for supporting the arm of a patient in a bent position of the upper arm relative to the lower arm.

BACKGROUND OF THE INVENTION

In surgical operations on the hand it is normally necessary in the postoperative phase to place the lower arm at rest in a bent position relative to the upper arm. Thus the lower arm of a lying patient is normally positioned upward at an angle of 90° relative to the upper arm, lest the hand be supplied with blood in an unnecessarily strong manner. Hitherto this rest position was obtained in the following manner: the lower arm was suspended by a support band on the plaster or on the bandage. The support band was suspended from above, e.g. from a supporting arm on the bed frame, located above the patient. However, this results in tractive forces on the lower arm that are felt as troublesome by the patient.

SUMMARY OF THE INVENTION

The task of the present innovation consists in making available a novel type of support arrangement with which the aforesaid disadvantages are avoided and which, in addition, can be produced simply and economically.

This task is accomplished with respect to the generic support arrangement by the fact that the support arrangement includes a holding bag, which on its upper side is attachable in a hanging manner to a support, and that the holding bag on the one hand forms on its lower side a rest for the upper arm and on the other hand forms on its side turned away from the upper arm a rest for the underside of the bent lower arm, so that the lower arm is not extensible within the holding bag or bendable in the direction of the upper arm.

The support arrangement according to the innovation has the advantage that, by virtue of the rest for the lower arm as well as the positioning of the lower arm through the holding bag, no troublesome tractive forces act on the lower arm or its bandage. Vascular congestion, etc. caused by the support is thereby avoided. Beyond that, the support arrangement can be produced with simple means in an economical manner.

By constructing the holding bag from a cut that is sewn up on the top side as well as on the bottom side, for one thing it can be manufactured in an especially simple manner, and for another thing it can be advantageously collapsed, i.e. folded, and thus stored without problem.

The tapered shape of the holding bag on its upper side ensures an optimized application of force from top to bottom, whereby the force on the lower-side rest acts evenly upon the upper arm.

Inasmuch as both sides of the holding bag in the tapered region are formed open, this holding bag can be threaded directly onto a holding rod and at the same time make possible a slight twisting of the bag with respect to the holding rod.

The ability to close the side of the holding bag facing the upper arm has the advantage that after the closing of this side of the arm, which on account of a plaster cast can have an excessive weight, it cannot move towards the upper arm, i.e. unintentionally fall towards the patient and injure him.

For the closing of the side facing the upper arm, provision is appropriately made for at least one cord. However, provision can also be made for at least one pair of cords, which pair consists in each case of one cord attached to each position of the holding bag, which cords are tied together for the closing.

Likewise, for suspending the holding bag from a support at least one fastening cord or pair of cords is appropriately provided for, by means of which cord or pair of cords the support arrangement can be fixed at different heights. In the case of a pair of fastening cords, this can consist of one shorter and one longer fastening cord, whereby a tying together can take place in an accessible and simple manner on the side and not on the upper side of the support.

If the fastening-cord pair is implemented on the underside of a seam that is located on the upper side of the holding bag, a more secure support of the holding bag is ensured, without requiring an expensive stitching or gluing of the cord to the holding bag.

The holding bag is appropriately to be positioned in such a manner that the lower arm located within maintains a lateral freedom of movement, whereby the supplying of blood to the arm placed at rest can be aided by small movements.

For increasing the strength of the holding bag it can be formed double-layered on the side facing the upper arm, preferably over the entire side, and/or on the open side-region of the side facing the lower arm. This leads, on the one hand, to a strengthening of the "open" edge region not sewn up with an opposite side, so that, for example, a tearing of the material is prevented. On the other hand the cords can also be securely attached to the double-layered side facing the upper arm, for example sewn onto it.

The holding bag consists appropriately of textile-like material, whereby it is usable many times and in addition can be cleaned in common within the framework of the usual hospital laundering process.

Appropriately, the length of the tapering region corresponds to approximately a third of the overall length of the holding bag. By this means the holding bag can be employed in one standard size, at least for adults.

BRIEF DESCRIPTION OF THE DRAWINGS

An appropriate configuration of the innovation will be explained in more detail in the following, with the aid of the drawn figures. They show:

FIG. 3: a cut of the holding bag

DETAILED DESCRIPTION OF PREFERRED EMBODIMENTS

Figure 1:
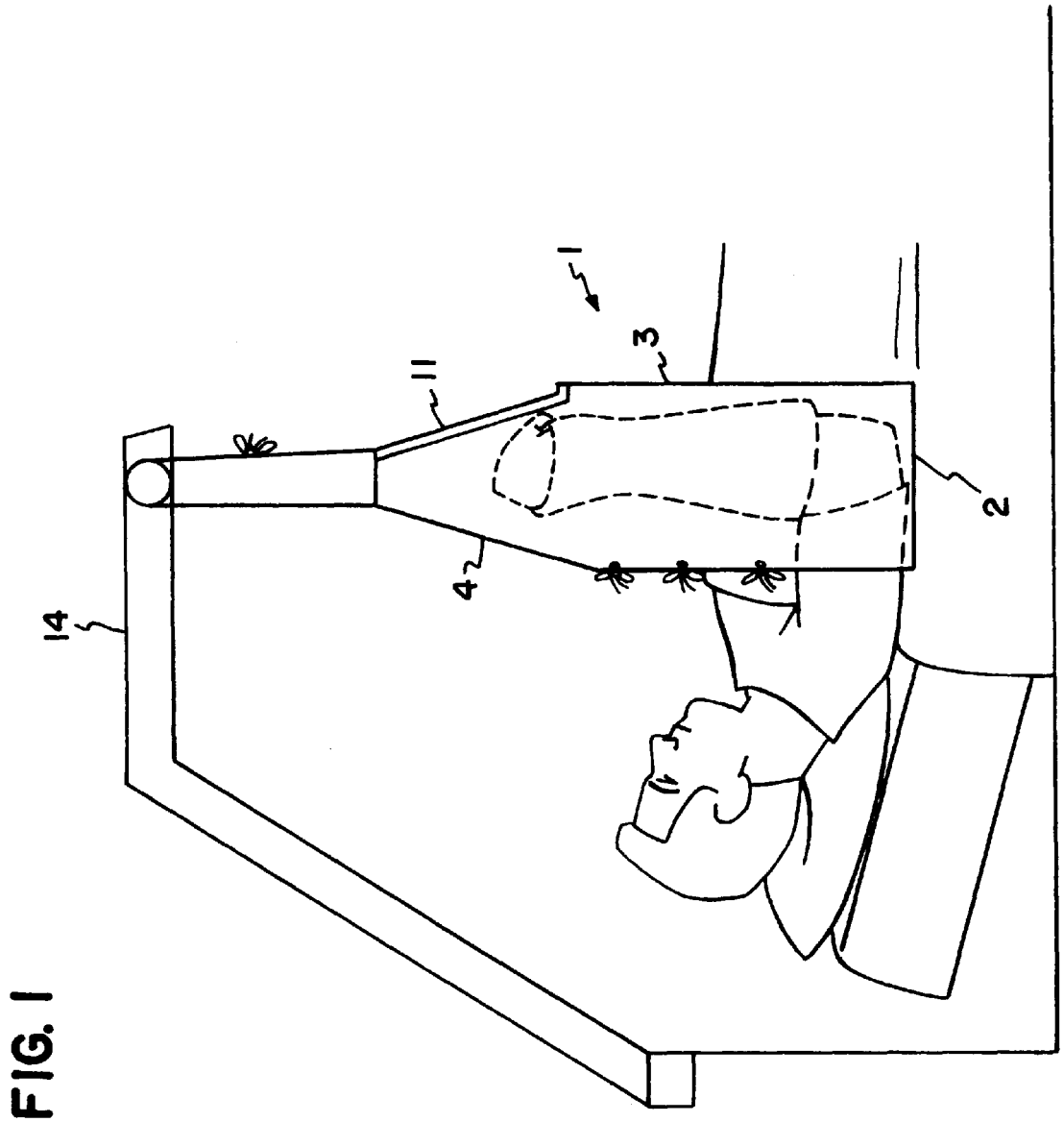
FIG. 1: a side view of the support arrangement in the applied state

FIG. 1 illustrates the application of the support arrangement at the sick-bed. The holding bag 1 is suspended by a fastening cord 12 from a support 14, which in turn is attached to the sick-bed. Here the upper arm of the patient rests upon the bottom side 2 of the holding bag 1, while the bent lower arm leans against the side 3 turned away from the upper arm. In this way the arm is supported and held in a manner that is secure and conducive to healing.

The upper side 11 of the holding bag 1 is distinguished by a form that is tapered upwards. This tape red or trapezoid-like upper side 11 corresponds to approximately a third of the overall length of the holding bag 1. This form effects an optimized introduction of force from the upper side 11 of the holding bag downwards, so that the force acts evenly upon the upper arm at the bottom side 2.

Figure 2:
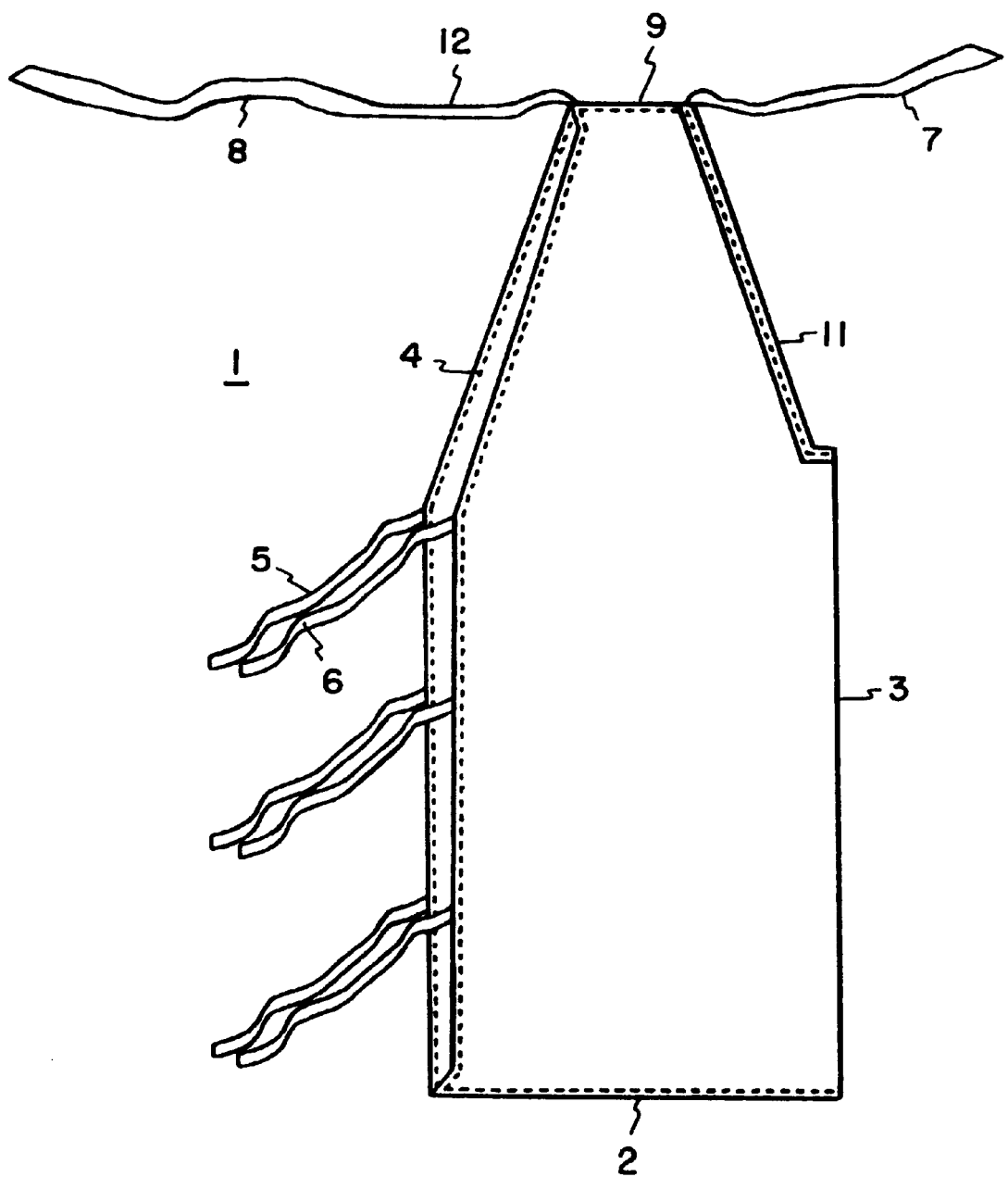
FIG. 2: a side view of the sewn-together holding bag

In FIG. 2, a more precise manner of viewing the holding bag 1 shows cords 5, 6 attached at each position to the side 4 facing the upper arm, whereby in each case two opposite cords 5, 6 can be joined together for a pair of cords.

A tying together of these cord pairs after the inserting of the arm prevents an unintended failing out of the arm in the direction of the patient's head. Also evident is a double-layered side 3 facing the upper arm, which side effects an increase in the strength of this partly open side and prevents a tearing of the edges attached at the side. The tapered region is also open on the side 3 facing the upper arm and is there formed likewise double-layered, in order to prevent, for example, a tearing when the lower arm is leaned against it.

The bottom side 2 of the holding bag 1 is sewn together and thus forms the rest for the upper arm. The upper side 11 of the holding bag 1 is likewise sewn together, with a fastening cord having been sewn into this seam 9. It is easily sewn on in one piece, since in this region both the side turned away from the upper arm and the side 4 facing the upper arm are open. A continuous cord 12 runs under the seam 9 and is fixed in such a manner that it forms on one side a shorter fastening cord 7 and on the other side a longer fastening cord 8. By this means a tying together of the two fastening-cord segments is possible in a simple and accessible manner at the side.

FIG. 3 shows the symmetrical cut 10 of the holding bag 1. By virtue of this symmetry, for one thing the cut 10 is easy to produce and for another it is simple to sew together, after one has folded it along the axis of symmetry 13. The V-shaped cut formed by the two trapezoid-like sections corresponds to the open side 3 turned away from the upper arm, this section—as already explained—being double-layered.

What is claimed is:

1. Support arrangement for supporting the arm of a patient in a bent position of the upper arm relative to the lower arm, wherein the support arrangement includes a holding bag (1), which on an upper side (11) is attachable in a hanging manner to a support (14), and wherein the holding bag (1) forms a lower side (2) configured for the upper arm, and forms a first side (3) configured for the underside of the bent lower arm, and wherein the holding bag (1) is made exclusively of textile material and consists of a flat cut (10), folded along an axis of symmetry (13) and sewn along the upper and lower sides, wherein an open second side (4) of the holding bag (1) comprises at least one cord for closing the second side (4), wherein the upper side comprises at least one one-piece fastening cord for fastening the holding bag (1) at the upper side and wherein the support arrangement further comprises a seam (9) on the upper side and said fastening cord is led through on an underside of the seam (9) for fastening the holding bag at the upper side.

2. Support arrangement according to claim 1, wherein the holding bag (1) has a width, the width tapering at least on the upper side (11).

3. Support arrangement according to claim 2, wherein the holding bag (1) forms openings adjacent the upper side (11) on both the first and second sides.

4. Support arrangement according to claim 3, wherein the holding bag (1) comprises two layers at the opening on the first side.

5. Support arrangement according to claim 2, wherein a region where the width tapers has a length that corresponds approximately to a third of an overall length of the holding bag (1).

6. Support arrangement according to claim 1, wherein the at least one cord for closing the second side (4) comprises at least one pair of cords, which pair is attached to the holding bag (1) at the second side.

7. Support arrangement according to claim 1, wherein the at least one one-piece fastening cord for fastening the holding bag (1) at the upper side comprises a pair of fastening cords, which pair consists of a shorter and a longer fastening cord (7 and 8 ) at the upper side.

8. Support arrangement according to claim 1, wherein the holding bag (1) is dimensioned in such a manner that a freedom of movement is ensured for the lower arm located within it.

9. Support arrangement according to claim 1, wherein the holding bag (1) comprises two layers over the entire second side (4).

* * * * *